US012797038B2

(12) United States Patent
Madar et al.

(10) Patent No.: US 12,797,038 B2
(45) Date of Patent: Nov. 17, 2026

(54) MEDICAL FOLLICLES ASSESSMENT DEVICE WITH ERGONOMIC GRIP

(71) Applicant: PULSENMORE LTD., Omer (IL)

(72) Inventors: Dotan Madar, Ashkelon (IL); Ravit Levy, Tel Aviv-Jaffa (IL); Minelu Sonnenschein, Meitar (IL); Naty Moskovich, Tel-Aviv (IL)

(73) Assignee: PULSENMORE LTD., Omer (IL)

( * ) Notice: Subject to any disclaimer, the term of this patent is extended or adjusted under 35 U.S.C. 154(b) by 0 days.

(21) Appl. No.: 19/120,046

(22) PCT Filed: Nov. 28, 2023

(86) PCT No.: PCT/IL2023/051218
§ 371 (c)(1),
(2) Date: Apr. 10, 2025

(87) PCT Pub. No.: WO2024/116175
PCT Pub. Date: Jun. 6, 2024

(65) Prior Publication Data

US 2026/0130638 A1 May 14, 2026

(30) Foreign Application Priority Data

Dec. 1, 2022 (IL) .......................................... 298736

(51) Int. Cl.

| | |
|---|---|
| ***A61B 8/12*** | (2006.01) |
| ***A61B 8/00*** | (2006.01) |
| ***A61B 8/08*** | (2006.01) |

(52) U.S. Cl.
CPC ................ *A61B 8/12* (2013.01); *A61B 8/085* (2013.01); *A61B 8/0858* (2013.01);
(Continued)

(58) Field of Classification Search
CPC ......... A61B 8/12; A61B 8/085; A61B 8/0858; A61B 8/4209; A61B 8/4455; A61B 8/461
See application file for complete search history.

(56) References Cited

U.S. PATENT DOCUMENTS 5,971,929 A * 10/1999 Sakamoto .............. A61B 8/445
600/462
11,413,018 B2 8/2022 Southard et al.
(Continued)

FOREIGN PATENT DOCUMENTS

CN 112617891 A 4/2021
DE 3636691 A1 * 5/1988 ................ B25J 9/08
WO 2022051637 A1 3/2022

OTHER PUBLICATIONS

The DE-3636691-A1 machine translation (Year: 1988).*
(Continued)

*Primary Examiner* — Alexei Bykhovski
(74) *Attorney, Agent, or Firm* — Hoffman Warnick LLC

(57) ABSTRACT

A device adapted to monitor the follicles and to assess the thickness of the endometrium of a subject, comprises: a) an elongated member having a tip that houses an ultrasound probe; and b) an ergonomic grip adapted to be held in the hand of a subject, said grip having a concave portion, the lowest point of which is located on an imaginary projection of the inner volume of said elongated member.

5 Claims, 5 Drawing Sheets

(52) U.S. Cl.
CPC .......... *A61B 8/4209* (2013.01); *A61B 8/4455* (2013.01); *A61B 8/461* (2013.01)

(56) References Cited

U.S. PATENT DOCUMENTS

| | | | | |
|---|---|---|---|---|
| 2018/0289416 | A1 | 10/2018 | Chee et al. | |
| 2020/0187906 | A1 | 6/2020 | Mienkina et al. | |
| 2023/0054353 | A1 * | 2/2023 | Robbins ............... | A61B 8/4488 |
| 2023/0139828 | A1 * | 5/2023 | Ridge .................. | A61B 8/4455 600/437 |

OTHER PUBLICATIONS

PCT International Search Report and Written Opinion for International Application No. PCT/IL2023/051218, dated Dec. 31, 2023, 9 pages.
Pereira Isabel et al: "Self-operated endovaginal telemonitoring: a prospective, clinical validation study", Fertility and Sterility, Elsevier, Amsterdam, NL, vol. 106, No. 2, Apr. 16, 2016 (Apr. 16, 2016), p. 306, XP029669737, ISSN: 0015-0282, DOI:10.1016/J.FERTNSTERT.2016.03.043 * "Study Protocol"figure 1 *.

* cited by examiner

MEDICAL FOLLICLES ASSESSMENT DEVICE WITH ERGONOMIC GRIP

FIELD OF THE INVENTION

The present invention relates to the field of medical devices. In particular, the invention relates to devices and a system for monitoring follicles and assessing the thickness of the endometrium.

BACKGROUND OF THE INVENTION

In vitro fertilization (IVF) is a method of assisted fertilization in which an egg is combined with sperm outside the body ("in vitro"). After natural ovulation or ovarian stimulation, IVF can be performed by collecting the contents from a woman's fallopian tubes or uterus. In most IVF procedures, the ovaries are stimulated to make the follicles grow and produce mature eggs. Ovarian follicles play a significant part in every IVF cycle; therefore, monitoring the development of ovarian follicles is a critical part of the IVF process. Nowadays, IVF patients undergo several pelvic (vaginal) ultrasound scans performed by specialized personnel, i.e., nurses or physicians, during the natural menstrual cycle or the ovarian stimulation phase to confirm that the dosage of medication given to them to promote ovulation is correct and to determine when they are ready for egg collection.

In addition, the thickness of the endometrium changes during a person's menstrual cycle, but other factors can also prompt changes. It is therefore critical in many cases to measure the tissue thickness. The endometrium is the lining of the uterus. It is one of the few organs in the human body that changes in size every month throughout a person's fertile years. Each month, as part of the menstrual cycle, the body prepares the endometrium to host an embryo. Endometrial thickness increases and decreases during the process. Two hormones, estrogen and progesterone, prompt these endometrial growth cycles, which are shed through menstruation if a pregnancy does not develop.

According to the Radiological Society of North America (RSNA), the endometrium is thinnest during menstruation, usually between 2-4 millimeters (mm) in thickness. The first half of the proliferative phase starts around days 6 to 14 of a person's cycle, or the time between the end of one menstrual cycle when the bleeding stops, and before ovulation. At this phase, the endometrium begins to thicken and may measure between 5-7 mm. As the cycle progresses and moves towards ovulation, the endometrium grows thicker, up to about 11 mm. About 14 days into a person's cycle, hormones trigger the release of an egg. Endometrial thickness is at its greatest during this secretory phase and can reach 16 mm. Endometrial thickness is important in pregnancy. Healthcare experts link the best chances for a healthy, full-term pregnancy to an endometrium that is neither too thin nor too thick. This allows the embryo to implant successfully and receive the nutrition it needs. The endometrium gets thicker as the pregnancy progresses. Thus, monitoring and measuring the thickness is critical to a successful IVF and also for fertility preservation.

The monitoring includes assessing the number and size of the follicles on each ovary by ultrasound and dedicated blood, saliva, or urine tests that measure the concentrations of relevant hormones. When the follicles are ready and are of the right size, around 18-20 mm, a trigger of hCG hormone injection is administrated. This trigger stimulates the follicles to discharge the mature eggs. Specialists then collect the mature eggs at a medical facility.

Because timing is essential in all IVF procedures, there is a need for daily monitoring of the ovarian follicles and the thickness of the endometrium, which creates a substantial burden on the patients and the medical personnel and equipment. It is therefore clear that it would be highly desirable to be able to obviate the need for frequent visits to the medical facility where the assessment of follicle development is performed, thus reducing the burden and costs on the patient and the system.

In pursuit of the abovementioned aim, devices were developed that substantially reduce the need to perform follicle monitoring and its assessment, as well as the thickness of the endometrium at a medical facility by specialized personnel, which is suitable to be used for assessment purposes for IVF and Embryo Transfer (IVF-ET), as well as other fertility-related procedures. These may include, for instance, monitoring of spontaneous ovulation, natural preservative procedures by determining when there is no danger of pregnancy, and any other medical process requiring such monitoring.

The abovementioned medical follicles assessment devices (referred to hereinafter as "MFA devices" for brevity) are the subject of co-pending Israeli patent application nos. 285798, filed Aug. 23, 2021, 293114, filed May 12, 2022, and 295946, filed Aug. 25, 2022, by the same applicant hereof, the full descriptions of which are incorporated herein by reference (hereinafter referred to as "earlier MFA devices" for convenience). An MFA device generally indicated by numeral 100 according to one embodiment of the abovementioned patent applications, is shown in FIG. 1. In this embodiment, grip 111 is provided with a portion 112 that, if desired, may contain an actuation switch, which operates the ultrasound probe located in tip 113. Since handle or grip 111 is held in the patient's hand during the operation of the ultrasound device, a simple application of pressure or release thereof turns the probe on or off, as the case may be.

The MFA device is adapted to identify follicle proprieties and the thickness of the endometrium. The MFA device is connected, wirelessly or via a wired connection, to a smartphone or the like smart device and allows a layman operator to produce ultrasound images without the need for a specialized ultrasound operator to be present in person, e.g., in the convenience of their home. The MFA device may connect to portable communication devices such as smartphones, tablets, or other suitable devices via wireless or wired connections. Wireless connections may include, for example, Bluetooth or Wi-Fi, WIFI 5/6/7/8, UWB (ultra-wideband), or the like. In one embodiment of the invention, the identification of follicles and the determination of the thickness of the endometrium are performed automatically using image processing and related processes. Alternatively, these determinations are carried out remotely by a specialist who inspects the images generated by the MFA device. Images are transferred to the smart device coupled with the MFA device of the invention via wire or wirelessly and then transmitted to the specialist for evaluation.

The MFA device enables obtaining valid clinical data by instructing the patient to move the MFA device in simple hand movements. Instructions can be provided in any suitable way, for instance, by voice instructions or video instructions that can be played or displayed, for instance, on a user's smart device. Accordingly, without the need for any technical background, patients can scan and automatically send the images to the physician or other technician.

As will be understood by the skilled person, the MFA device of the invention has a defined grip, which also defines the position of the ultrasound probe. For instance, when holding handle 111 of the MFA device of FIG. 1, the probe's rotation is limited by the movement of the user's hand and, therefore, the direction in which the probe is scanning is essentially defined, as opposed to the prior art MFA devices in which the elongated member may rotate freely and as such just by looking at the images acquired, it is not possible to know whether scanning took place along a vertical, horizontal, or intermediate line.

As used herein, "monitoring" refers to visual inspection and parameter measurements, as the case may be. For instance, monitoring the development of follicles will, in many cases, involve measuring their size, as when IVF procedures are involved, but in some cases, it may be sufficient to ascertain qualitatively that follicles are developing, as may be, for example, in some instances where natural ovulation is to be confirmed, even though the measurement of follicles size may be desirable or necessary also when monitory natural ovulation. The same applies to the monitoring of the endometrium.

Therefore, providing means by which the user can operate the monitoring MFA device safely and conveniently is also an important factor in the success of the monitoring. An improved user experience can be provided by allowing the user to self-control the depth of introduction of the MFA device, such that it is not insufficient, which may adversely affect the quality of the recorded images, and not too deep, which may be unsafe.

Furthermore, allowing a user to choose the angle at which the MFA device is held in the user's hand relative to the axis of penetration of the MFA device may also contribute to the user's experience and the monitoring quality.

The earlier MFA devices provide a significant advance in the field of IVF and give a solution to the abovementioned problems, thereby improving the procedure's quality and rendering a difficult process more accessible for the subjects. However, in the quest for further improving the procedure's outcome and patient compliance, the inventors have surprisingly found that an ergonomically designed grip significantly improves patient response and the quality of the ultrasound scans performed by the patient. This result is surprising since the grip shown at 111 in FIG. 1 is broadly recognized as the best grip shape for various devices and manipulations.

It is therefore an object of the present application to provide a follicles and endometrium thickness monitoring device that further improves on the earlier MFA devices.

It is a further object of the invention to provide a follicles and endometrium thickness monitoring device that is comfortable and easy to manipulate by an unskilled patient.

It is yet another object of the invention to provide an improved MFA device that can be useful and easy to use for monitoring during various stages of the menstrual cycle, as well as an aid in other fertility procedures.

Other objects and advantages of the invention will become a parent as the description proceeds.

SUMMARY OF THE INVENTION

The invention relates to a device adapted to monitor the follicles and to assess the thickness of the endometrium of a subject, comprising:

a) an elongated member having a tip that houses an ultrasound probe; and
b) an ergonomic grip adapted to be held in the hand of a subject, said grip having a concave portion, the lowest point of which is located on an imaginary projection of the inner volume of said elongated member.

In embodiments of the invention, the device comprises a depth-limiting element, which may be made of one piece, e.g., may be a rubber ring or can be made of other suitable material. In some embodiments, the depth-limiting element comprises two partial rings hinged together and a clamp suitable to connect them. The depth-limiting element may also comprise an elastomeric friction-generating layer.

The invention also encompasses a system for monitoring the follicles and assessing the thickness of the endometrium of a subject, comprising:

i) a device according to the invention;
ii) a smart device adapted to display to a user information relative to the operation of the device; and communication elements adapted to perform communication and transfer of data between the device and the smart device.

DETAILED DESCRIPTION OF THE INVENTION

Figure 1:
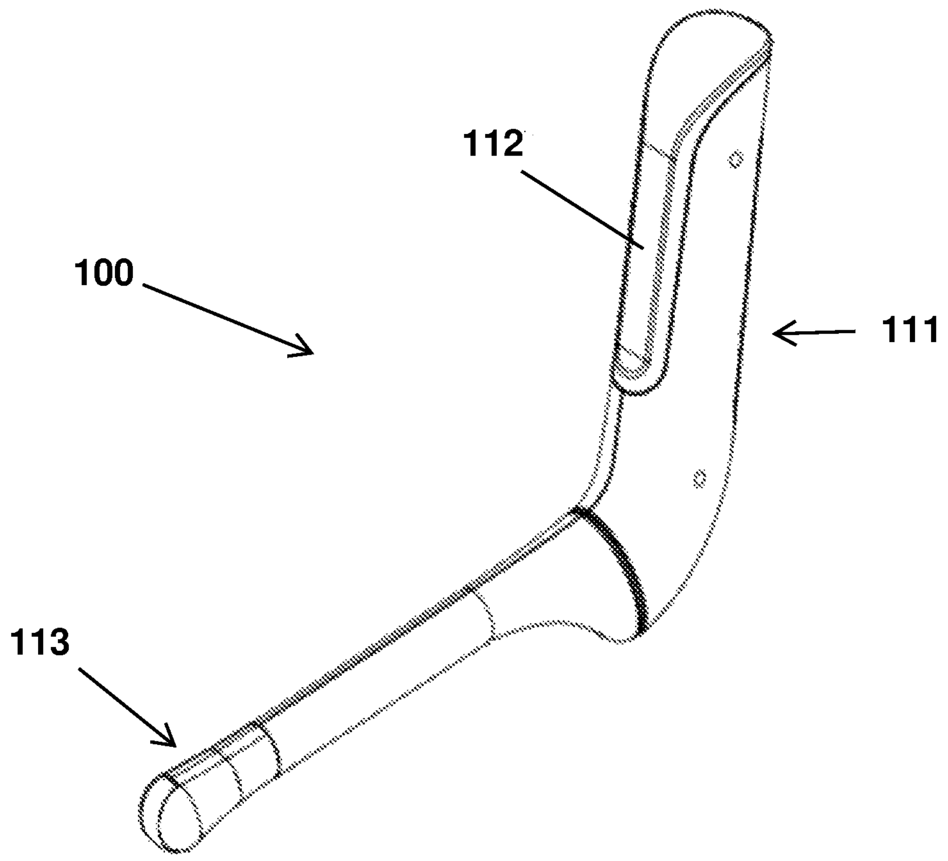
FIG. 1 shows an illustrative example of an earlier MFA device.

The MFA device is adapted to identify follicle proprieties and the thickness of the endometrium and possesses all the elements and components referred to above with reference to IL285798, IL293114, and IL295946 and in the description thereof. FIG. 2 (A and B) shows an MFA device 200 according to one embodiment of the invention, viewed from two different directions, with an ultrasound probe housed in tip 201 located at the distal end of the MFA device and of the elongated member 202 thereof, which is to be inserted in the vagina for ultrasound scanning. Like in the MFA device of FIG. 1, a handle or grip 203 is the portion the user holds during scanning. Grip 203 may hold various components of the system, such as communication elements, image processing, and power supply, which are not discussed herein in detail for the sake of brevity since they do not influence the mechanical elements of the invention. Similarly, elongated member 202 may contain wiring or wireless components to transmit data generated by the ultrasound probe to the handle or an external device. In some embodiments, i.e., particularly in a wireless device, a pressure switch 204 is provided to power the MFA device on and allow for ultrasound scanning. In some other embodiments, when the MFA device is connected by wires to a smart device such as a smartphone, no internal battery is needed in the MFA device, which is controlled by an app running on the smart device and powered by the smart device's battery. A depth-limiting element 205 is also shown in FIG. 2, which is novel and may be used alone or in conjunction with scale 206, as further discussed hereinafter. Moreover, in some embodiments, a pressure sensor is located at the distal tip of the device.

Pressure readings allow the user to determine whether the device has been introduced at a depth greater than advisable and, in some embodiments, to alert the user if undesirable pressure is being applied by the tip of the device. This may happen, for instance, even though the user has employed a depth-limiting element if the original depth that was set was incorrect, or if the element has moved inadvertently. Of course, as will be apparent to the skilled person, any other suitable method can be employed, such as light measurements, distance measurement using ultrasound, and any other proximity sensor instead of a pressure sensor.

Figure 2A:
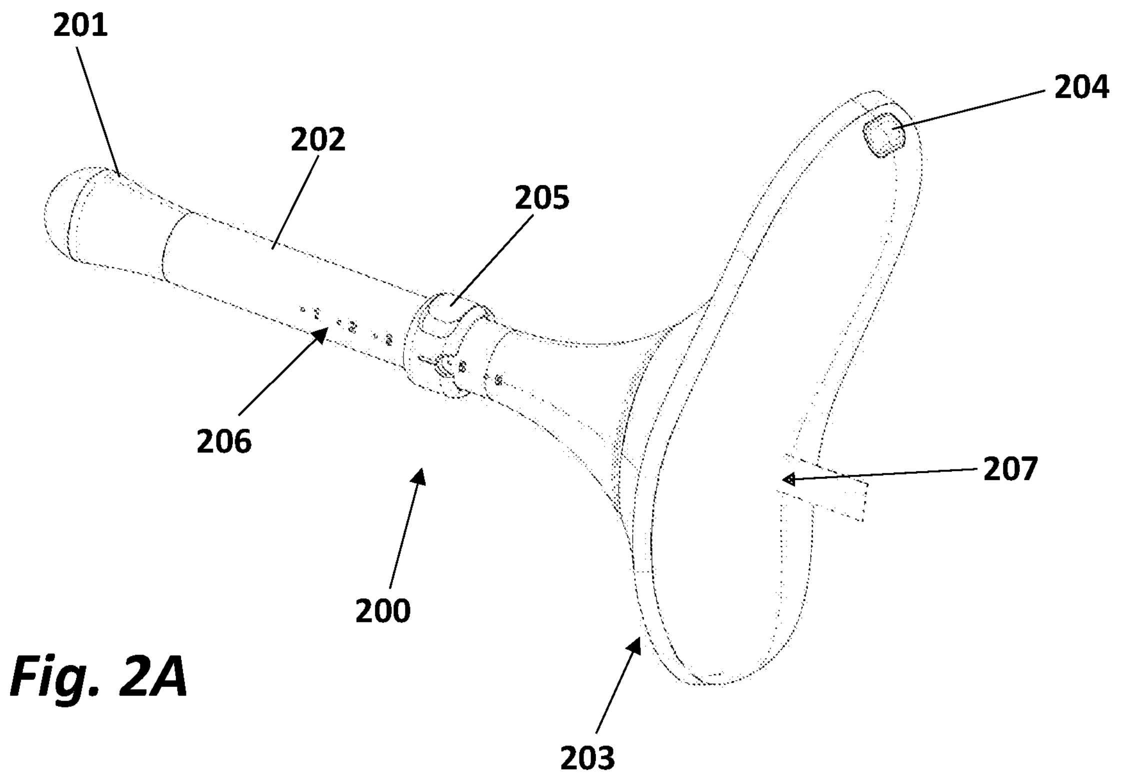
FIG. 2 (A and B) are perspective views of a wireless MFA device according to an embodiment of the invention.

Unlike the grip of the MFA device of the prior art, as exemplified in FIG. 1, in the MFA device of FIG. 2 (A and B), the grip 203 is not essentially tubular but rather is ergonomically shaped to possess a concave portion, the lowest point (or saddle) 207 of which is located on an imaginary projection of the inner volume of elongated member 202. This is a highly counter-intuitive and surprising structure for the handle of an intraluminal ultrasound device, as will be further discussed hereinafter, and thus prior art devices employ handles of the type shown in FIG. 1. This is further illustrated with reference to FIG. 3. The imaginary projection of the inner volume of elongated member 202 is indicated by the numeral 300, and it meets saddle 207, as explained above. As seen in the cross-section of FIG. 3, grip 203 can also house electronic components needed for operating the ultrasound probe or communicating with external devices, either wirelessly or through a wired connection. Said electronic components may vary according to the specific needs of different MFA devices and are well within the scope of the skilled person; therefore, the electronic parts are not discussed in detail for the sake of brevity, and some such elements are shown only for illustration.

Figure 2B:
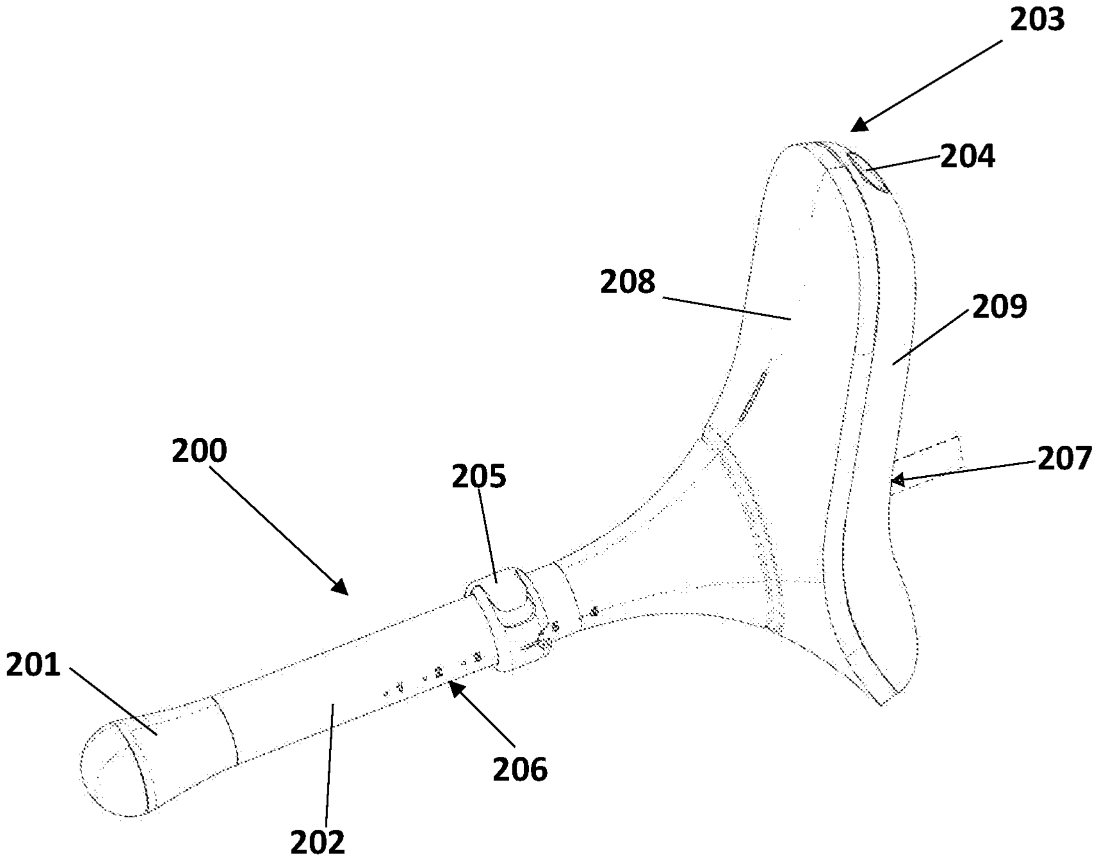
Figure 3:
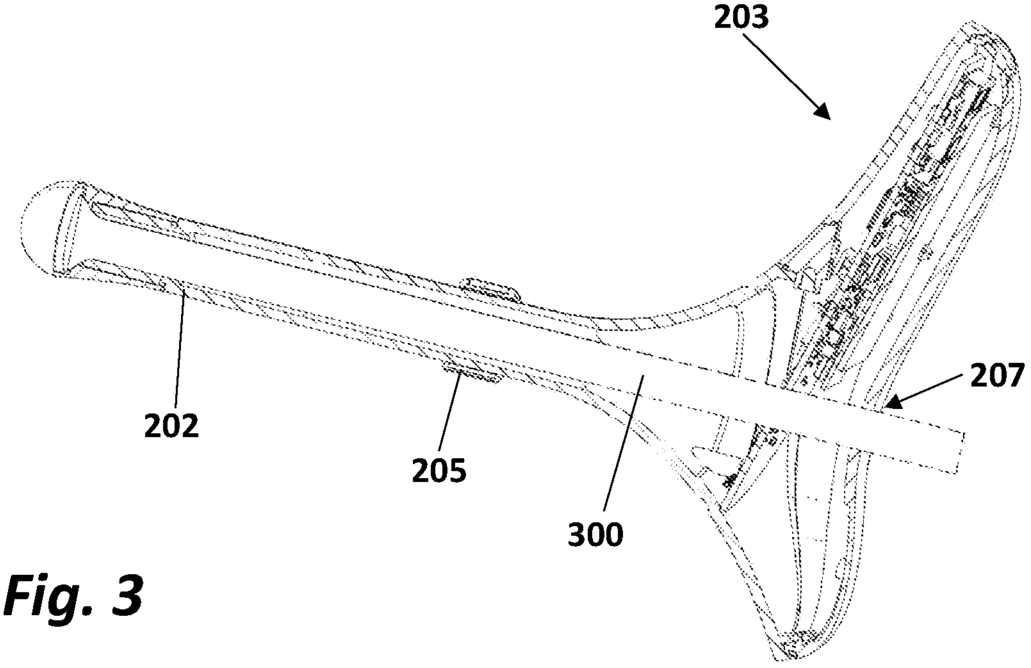
FIG. 3 is a cross-section of an MFA device of FIG. 2.
Figure 4:
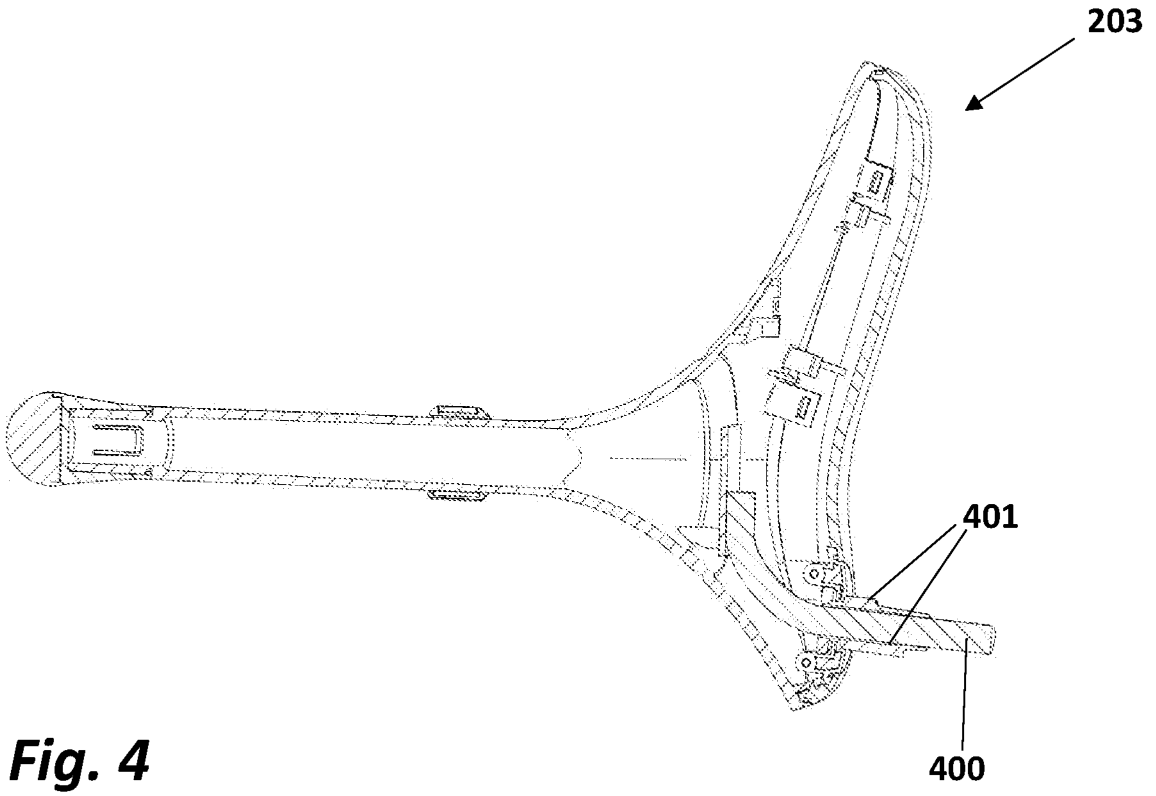
FIG. 4 is a cross-section of a wired MFA device according to another embodiment of the invention.

The embodiment shown in FIGS. 2 and 3 is a wireless MFA device. An embodiment of a wired MFA device is shown in FIG. 4, in which a segment of wire 400 is seen to exit grip 203 via wire guide 401. Wire 400 may be used to communicate with an external device, such as a PC, a tablet, or a cellphone, to supply power to the MFA device from a remote power source, or for any other purpose.

As clearly seen in the embodiment of FIG. 2B, grip 203 is made in some embodiments of two parts: a mean body part 208 and a lid 209, which can be removed to access the electronic components contained within the grip. The two parts can be kept together by mechanical pressure, as commonly done in the art of plastic materials, which needs no further discussion, or by any other known fastening elements.

Furthermore, in some embodiments, lid 209 can be manufactured to present a soft and even somewhat elastic surface to provide more comfort to the grip holder.

Figure 5:
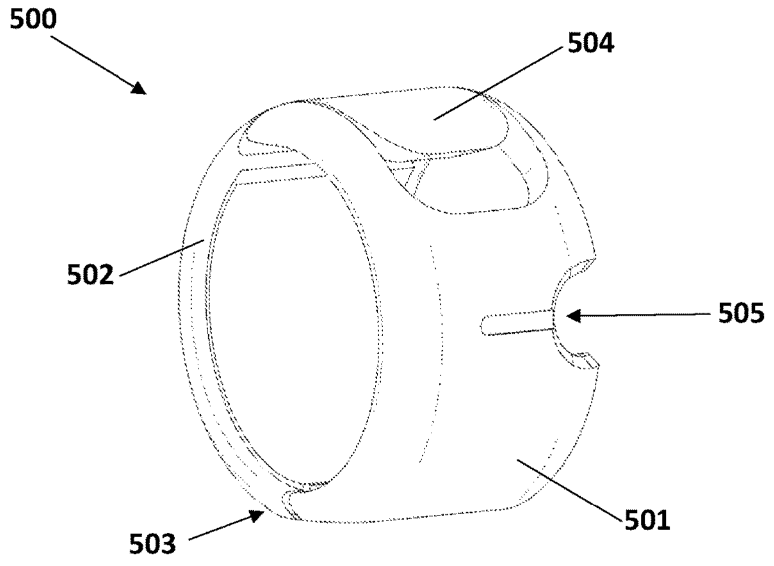
FIG. 5 shows a depth-limiting ring according to an embodiment of the invention.

FIG. 5 shows a depth limiting ring 500, which is seen in operation in FIG. 2B. In this particular embodiment, the ring has two parts, 501 and 502 (but can also be made in one piece, e.g., may be a ring made of rubber or other material), connected by a hinge 503 (not seen) and a clasp 504 that fixes part 501 and 502 together onto elongated member 202, thus applying a pressure that prevents ring 205 from moving. In some embodiments, an elastomeric layer can be added to the inside surface of the ring to increase friction and stabilize ring 205. The ring's presence, with its larger diameter, limits the depth of the probe's introduction.

Furthermore, in this particular embodiment, notch 505 is provided, which allows an easy reading of the scale 206 of FIG. 2, making it easy for the user to position ring 205 constantly at the same location.

Figure 6:
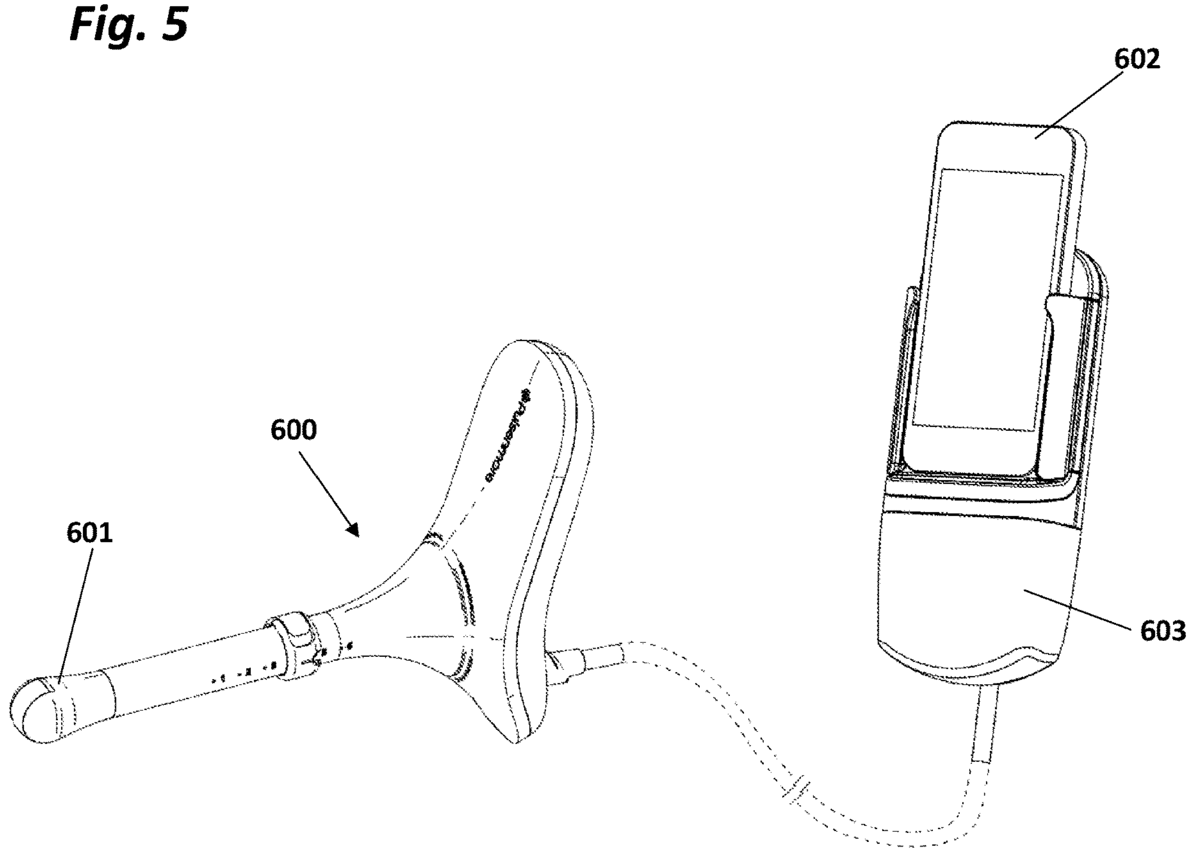
FIG. 6 schematically shows a wired system according to the invention.

FIG. 6 shows the operation of the MFA device of the invention in conjunction with a smart device. In this figure, an MFA device with a wired connection is seen. However, when a wireless MFA device is used, the connecting wire is simply omitted, and the following description applies mutatis mutandis. The MFA device 600 is as described with reference to the previous figures. It is operated by inserting it vaginally until the ultrasound probe contained in tip 601 is positioned at the desired location. Images generated by the ultrasound probe are transmitted to smart device 602, which in this embodiment is held in cradle 603, and in a wireless embodiment, are transmitted wirelessly to it. The cradle may contain, besides electronics needed to communicate with MFA device 600, also electronic elements allowing it to communicate with smart device 602, both to display images acquired by the ultrasound probe and to perform any other function that may be appropriate, such as imparting instructions to the user, allowing a remotely located health professional to communicate with the user and to guide the user in the operation of the MFA device, operating as a relay to remote stations, etc. When the connection is wireless, in embodiments of the invention and depending on the smart device employed, the cradle can be dispensed with, and MFA device 600 may be in direct wireless communication with smart device 602.

Figure 7A:
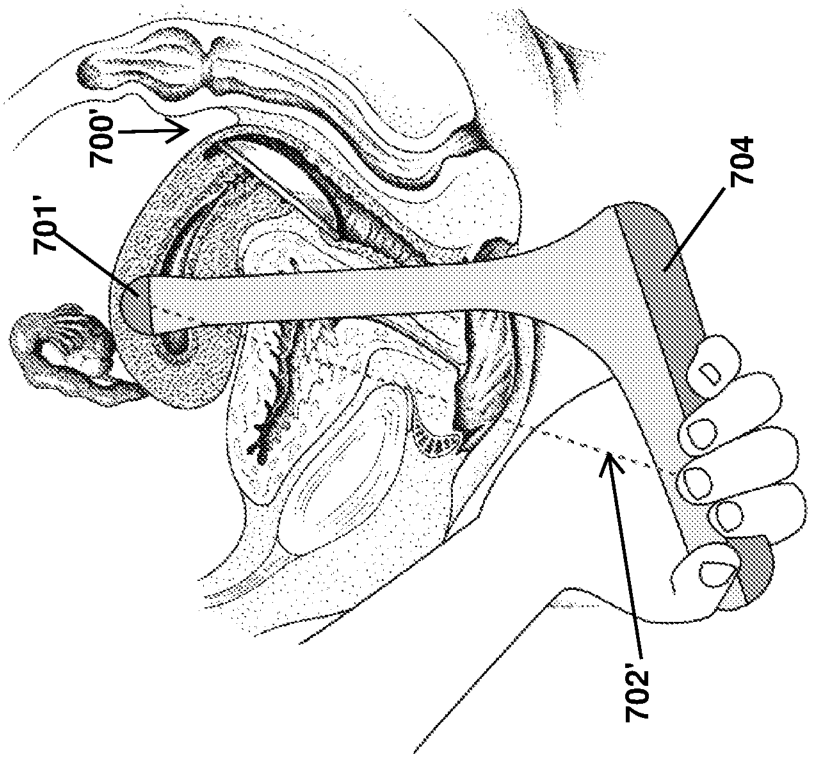
FIG. 7 illustrates the importance of the invention to a home user.
Figure 7B:
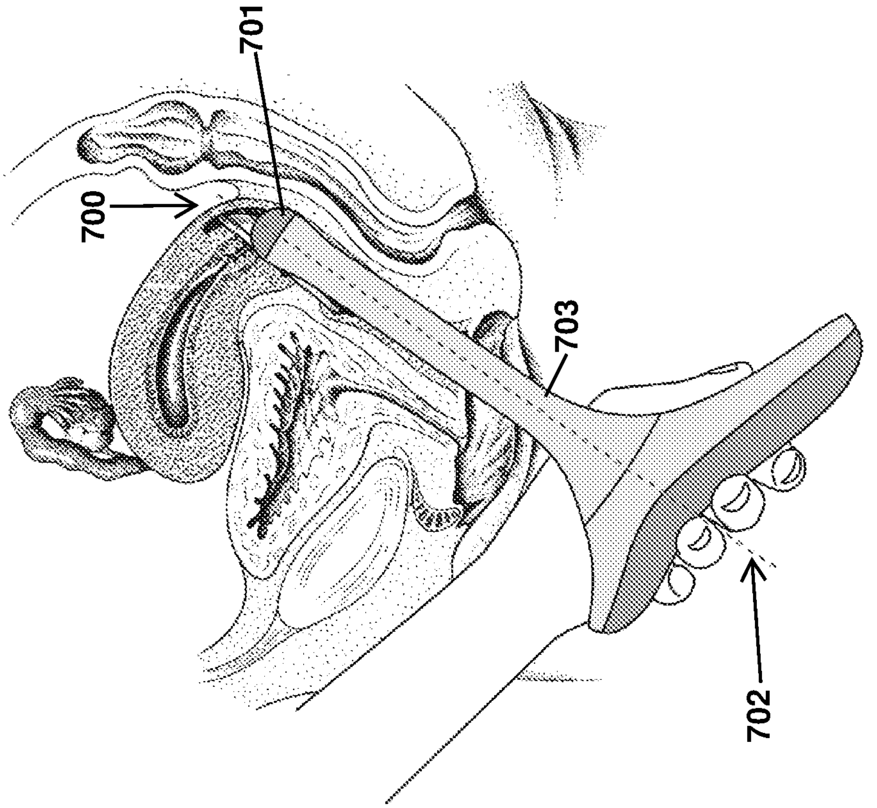

Referring now to FIG. 7, an important advantage of the invention is shown during operation (FIG. 7B) as compared with the prior art (FIG. 7A). When using a device of the invention, the location where the user applies a pressure that directs the tip 701 of the MFA device to the desired location 700, is located on axis 702 situated in the center of symmetry of elongated member 703. This allows the user to cognitively connect naturally with the location of tip 701 and, thus, to direct it easily to the correct location 700. In contrast, when using a grip 704 according to the prior art, as in FIG. 7A, there is a disconnect between the user's hand and the tip 701' of the MFA device. A movement of the user's hand does not result in a linear movement of tip 701' since the imaginary dotted line 702' does not pass simultaneously directly through the user's hand and elongated member 703'. This makes it harder for the user to correctly position tip 701' against location 700'. The grip of the invention results in an easier and more comfortable operation for the user in performing a procedure which, in itself, is unpleasant and inconvenient. Users report substantially less time required for the procedure, with fewer irrelevant or wrong readings than when operating with a device according to the prior art.

All the above description of embodiments of the invention has been provided for the purpose of illustration and is not meant to limit the invention in any way. Many modifications can be made to the various elements of the invention; for instance, different shapes can be provided for the ergonomic grip, employing various materials, all without exceeding the scope of the invention.

The invention claimed is:

1. A follicle and endometrium monitoring device, comprising:

a) an elongated member having a tip that houses an ultrasound probe; and b) a grip having a concave portion, the saddle point of said concave portion intersected by an imaginary projection of a longitudinal axis of said elongated member.

2. The device according to claim 1, further comprising a depth-limiting element.

3. The device of claim 2, wherein the depth-limiting element comprises two partial rings hinged together, and a clamp suitable to connect them.

4. The device of claim 2, wherein the depth-limiting element comprises an elastomeric friction-generating layer.

5. A system comprising:

i) the device of claim 1, ii) a smart device adapted to display to a user of the device information relative to the operation of the device; and iii) communication elements adapted to perform communication and transfer of data between the device and the smart device.

* * * * *